(12) United States Patent
Frankle et al.

(10) Patent No.: US 8,425,513 B2
(45) Date of Patent: Apr. 23, 2013

(54) METHOD AND SYSTEM FOR THE INTRAMEDULLARY FIXATION OF A FRACTURED BONE

(75) Inventors: Mark Allen Frankle, Tampa, FL (US); Sergio Gutierrez, Tampa, FL (US)

(73) Assignee: Clavicle, LLC, Tampa, FL (US)

( * ) Notice: Subject to any disclaimer, the term of this patent is extended or adjusted under 35 U.S.C. 154(b) by 992 days.

(21) Appl. No.: 12/410,367

(22) Filed: Mar. 24, 2009

(65) Prior Publication Data

US 2010/0137865 A1  Jun. 3, 2010

Related U.S. Application Data

(60) Provisional application No. 61/039,092, filed on Mar. 24, 2008.

(51) Int. Cl.
*A61B 17/56* (2006.01)

(52) U.S. Cl.
USPC ............................................. 606/63; 606/71

(58) Field of Classification Search .............. 606/62–68, 606/291, 323, 328, 70, 71
See application file for complete search history.

(56) References Cited

U.S. PATENT DOCUMENTS

| | | | |
|---|---|---|---|
| 5,484,439 A * | 1/1996 | Olson et al. | 606/65 |
| 6,916,323 B2 * | 7/2005 | Kitchens | 606/86 R |
| 2005/0107796 A1 * | 5/2005 | Gerlach et al. | 606/69 |
| 2010/0130978 A1 | 5/2010 | Orbay et al. | |

OTHER PUBLICATIONS

Orbay, Jorge L., Implate Wrist Arthrodesis Nail, Surgical Technique Guide, 2010 Skeletal Dyanmics LLC, Miami FL, US.
Orbay, Jorge L., Align Radial Head System, Surgical Technique Guide, 2011 Skeletal Dyanmics LLC, Miami FL, US.

\* cited by examiner

*Primary Examiner* — Eduardo C Robert
*Assistant Examiner* — Tara Carter
(74) *Attorney, Agent, or Firm* — Buchanan Nipper

(57) ABSTRACT

The system and method for intramedullary plate fixation of the preferred embodiments include a first intramedullary plate of a first geometry with a plurality of bores, a second intramedullary plate of a second geometry with a plurality of bores, a plurality of fasteners that fasten the first and second intramedullary plates to bone, and an alignment fixture held outside of the body that indicate the location of the bores of the first and second intramedullary plates and through which the fasteners are aligned with the bores of the first and second intramedullary plates, allowing the surgeon to make incisions in the patients body in known locations of the bores, and thus allowing for a minimally invasive intramedullary plate installation and fixation procedure.

15 Claims, 13 Drawing Sheets

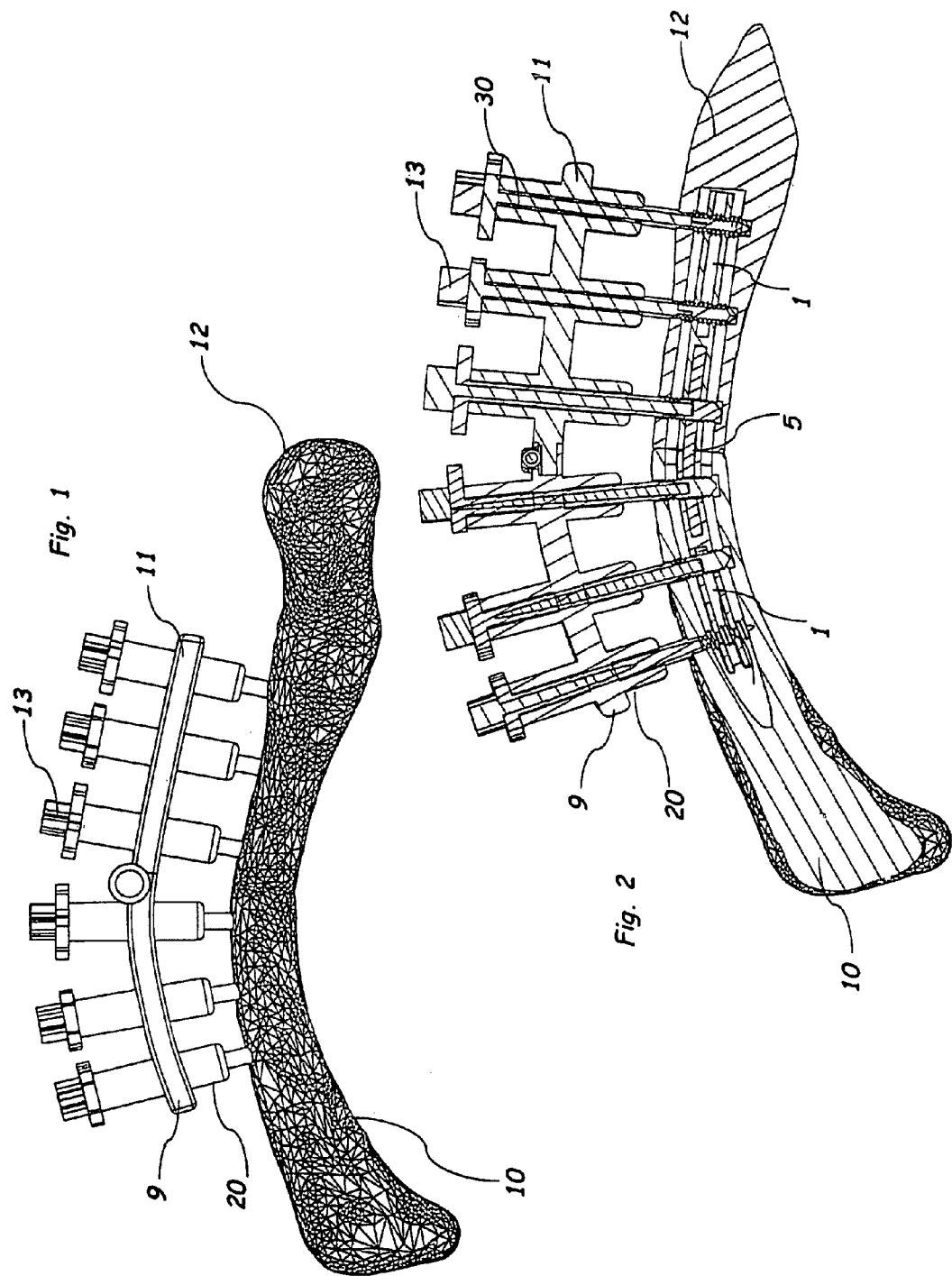

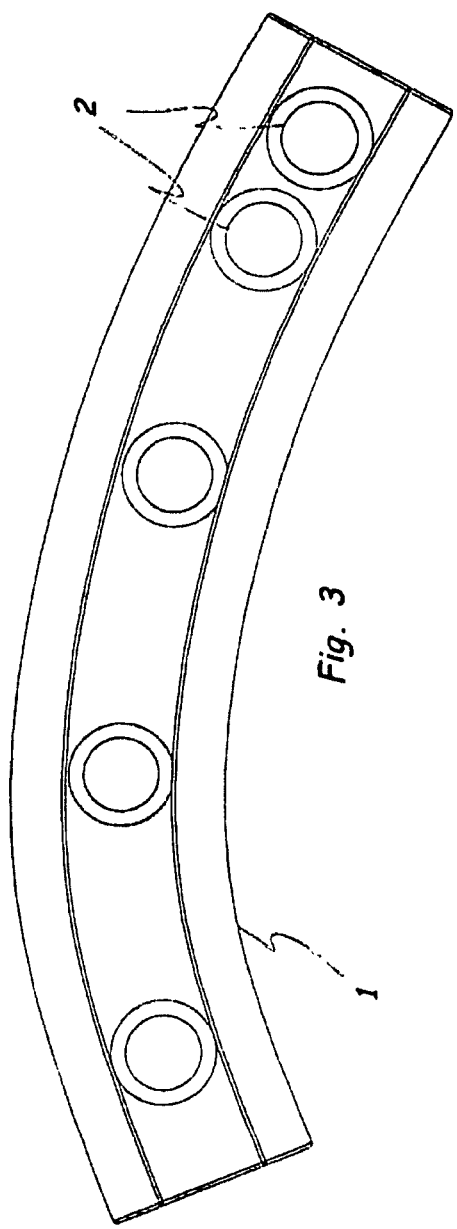

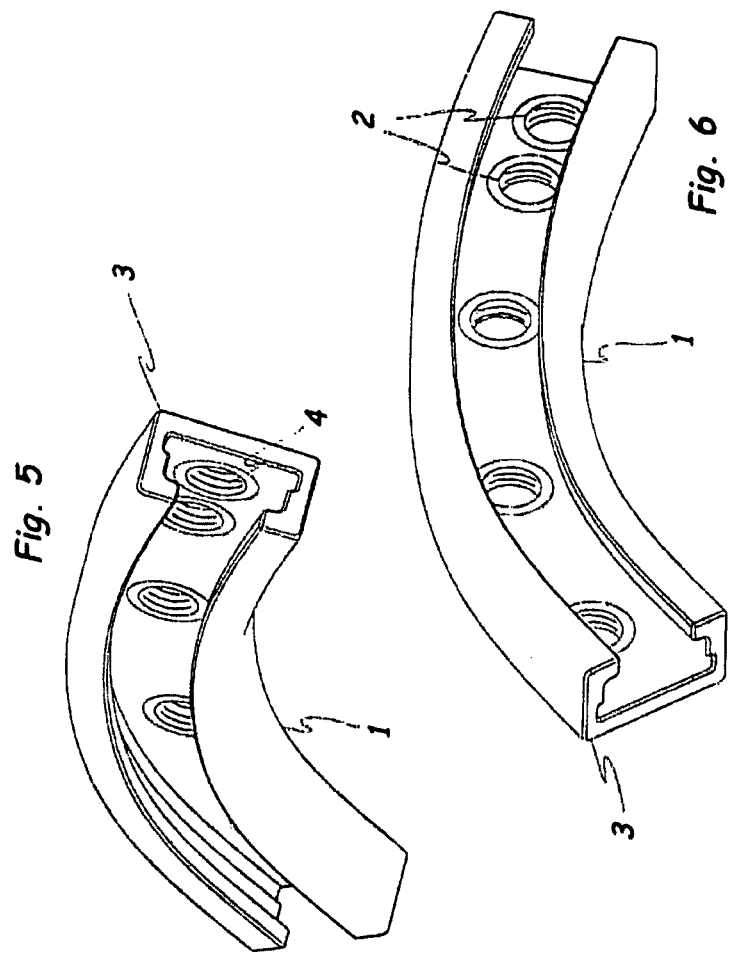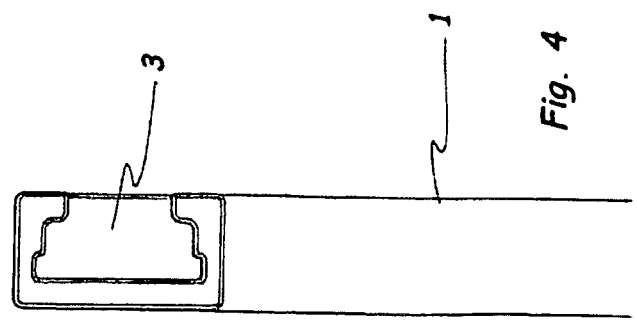

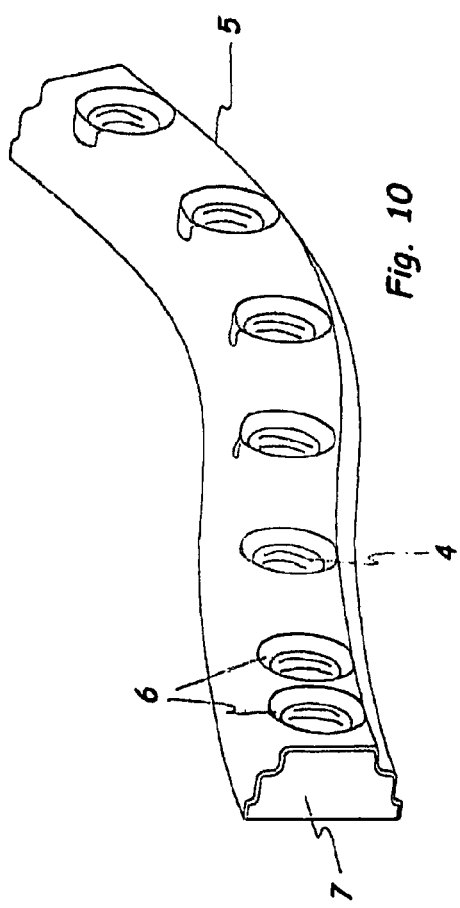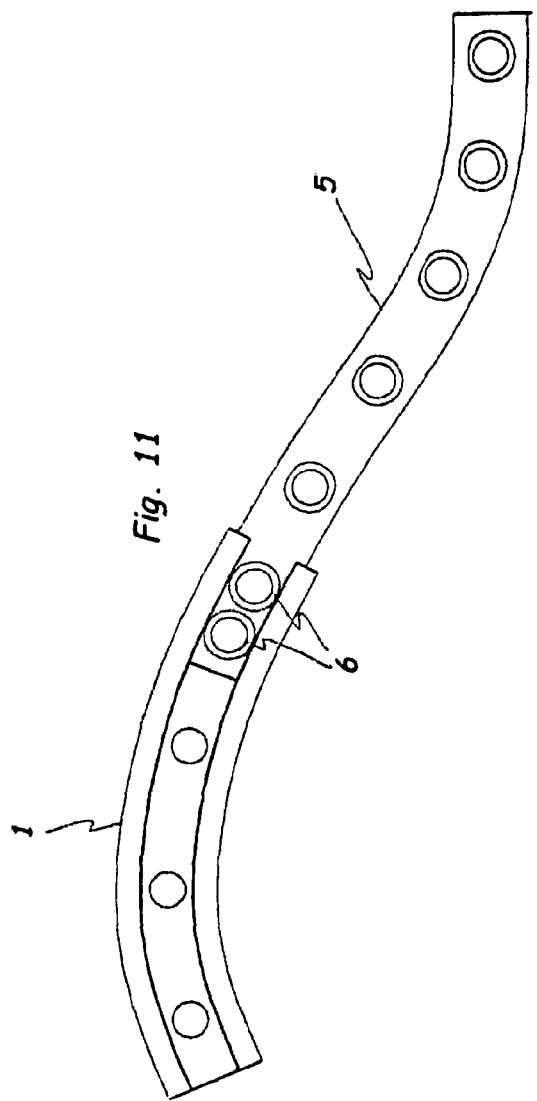

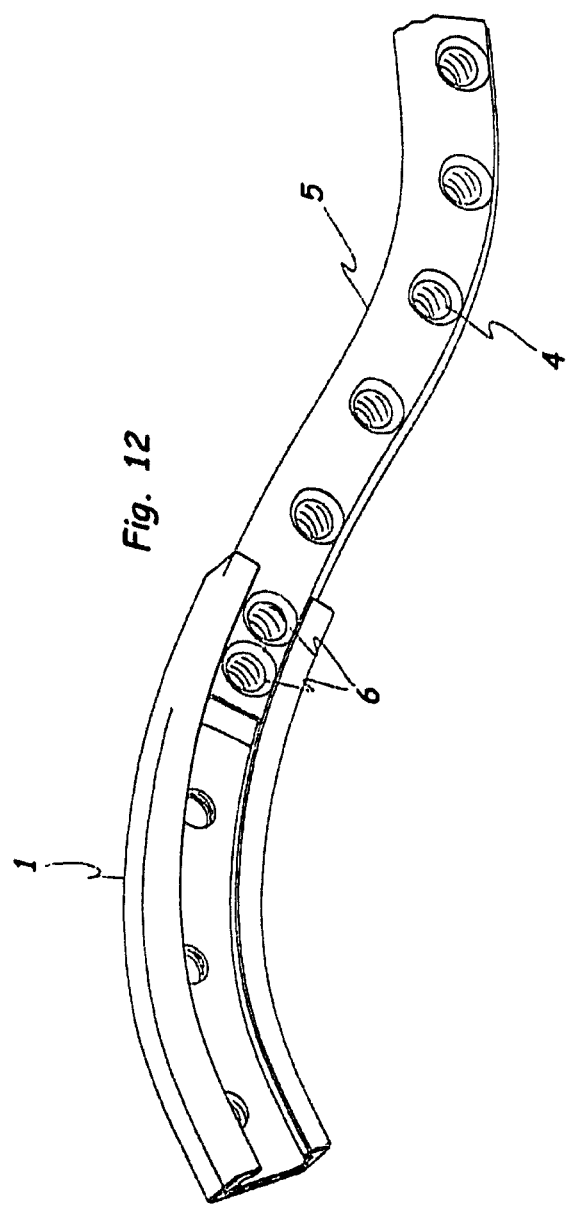

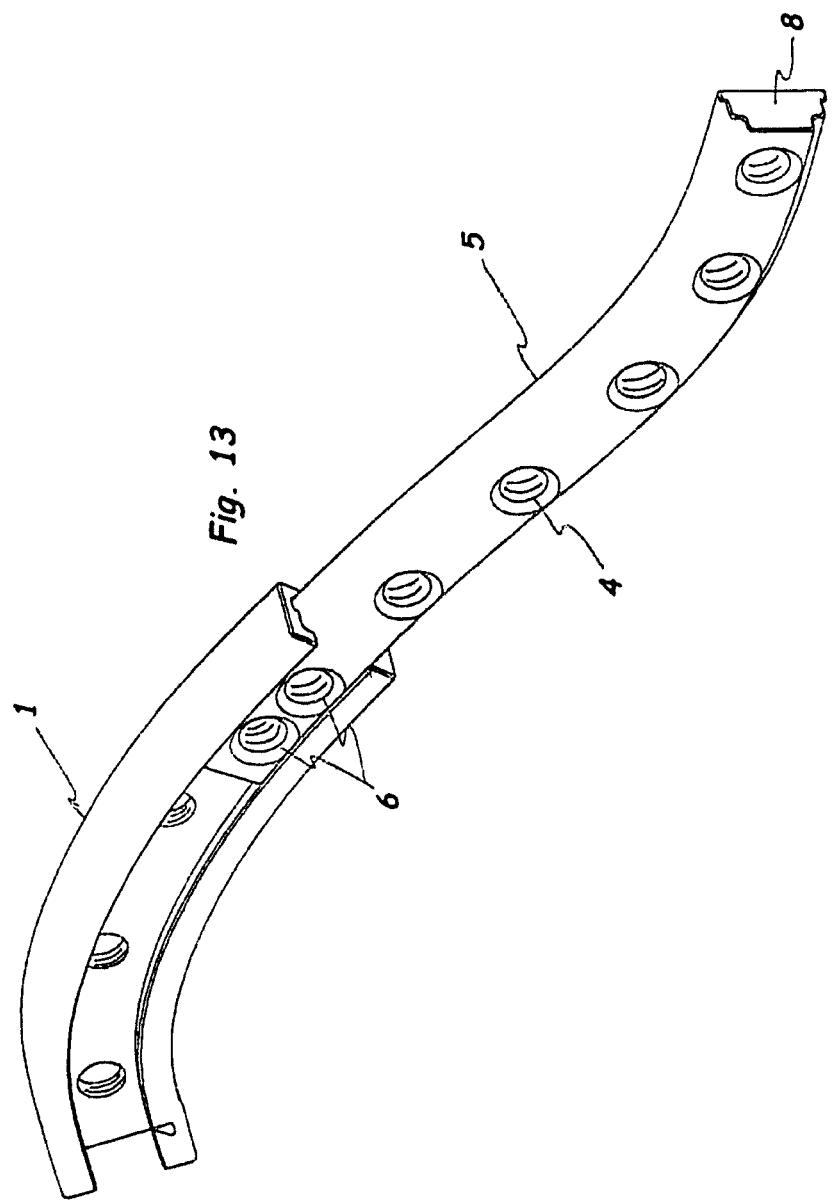

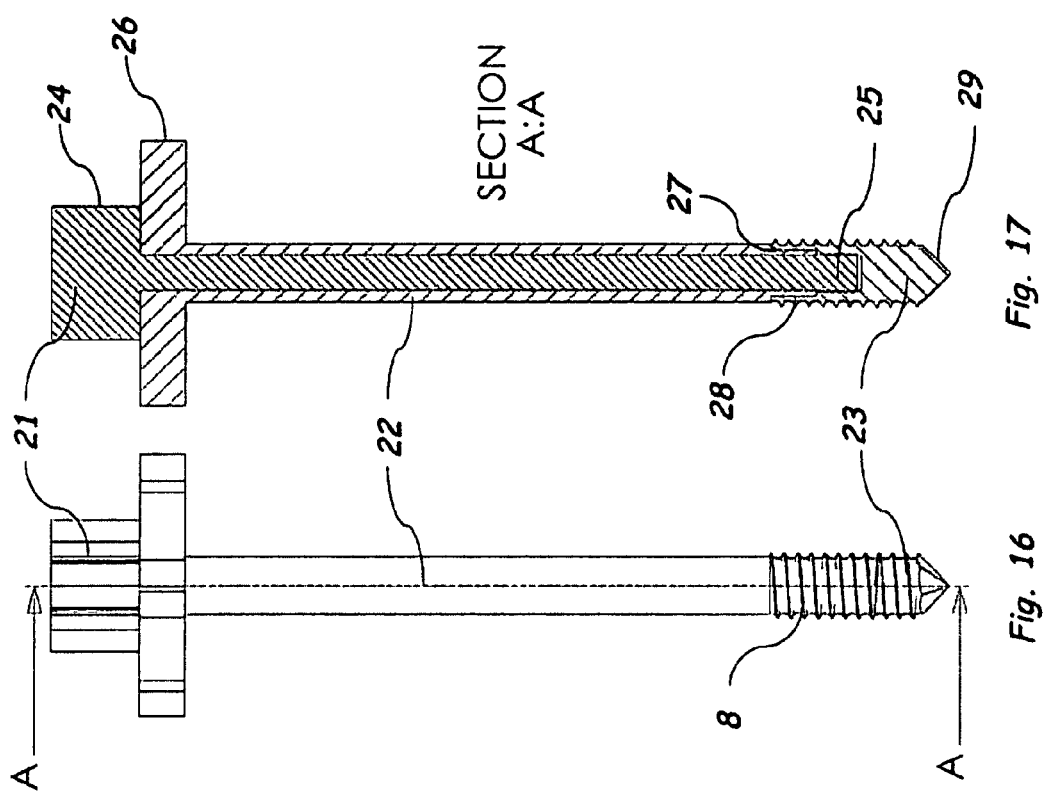

METHOD AND SYSTEM FOR THE INTRAMEDULLARY FIXATION OF A FRACTURED BONE

CROSS-REFERENCE TO RELATED APPLICATIONS

This application claims the benefit of U.S. Provisional Application No. 61/039,092, filed 24 Mar. 2008, which is incorporated in its entirety by this reference.

TECHNICAL FIELD

This invention relates generally to the field of bone fracture fixation, and more specifically to a new and useful method and system for the intramedullary fixation of a fractured bone.

BACKGROUND

Severe bone fractures are most commonly repaired with open reduction and internal fixation using plates and screws attached to the periosteum of the bone. The typical method to gain access to the fracture site is by making a large incision through the skin and muscles. Once the fracture has been exposed, the plate is then attached to the bone fragment(s) using screws. The placement of the bone plate aides in the healing of the fractured bone by minimizing the amount of interfragmentary movement. After the plate is in place, the wound is suture closed. The suture, however, often leaves behind a large scar.

Less severe bone fractures are usually treated using cast immobilization. This form of treatment, although effective in extremity fractures, is not ideal for fractures located in difficult to cast places (e.g., clavicle and ribs). The alternative is to forego the cast and allow natural healing to occur with limited use of the affected region.

Intramedullary plate fixation includes installing fixation plates inside the intramedullary canal of the fractured bone and is currently used as an alternative to periostial plate fixation and casting that yields reliable bone fracture healing. Intramedullary plate fixation also aids the surgeon in more accurately restoring the shape of the fractured bone to its original (pre-fracture shape) with the help of the anatomic shape of the plate. By utilizing the intramedullary canal for the location of the plate, intramedullary plate fixation provides for the lowest possible profile of fixation, minimizing problems of prominent hardware, as well as providing ideal mechanical resistance to forces across the fixation-bone interfaces. However, current intramedullary plate fixation procedures generally require a long incision to be made in the patient at the site of the fracture for the installation of the plates and the fixation of the plates using screws through the patient's bone. Additionally, intramedullary plates may have bore geometry that accommodates for screws or nails for fixation, but are not visible to the surgeon once the plates have been installed inside the intramedullary canal, thus complicating fixation procedures.

Thus, there is a need in the field of bone fracture healing to create a new and useful system and method for the intramedullary fixation of a fractured bone. This invention provides such a new and useful method and system.

BRIEF DESCRIPTION OF THE FIGURES

FIGS. 1 and 2 include a side view and a cross-sectional view, respectively, of a preferred embodiment of the invention being applied to a fractured bone;

FIGS. 3-6 include a front view, a cross-sectional view, a first perspective view, and a second perspective view, respectively, of the first intramedullary plate of the preferred embodiment;

FIGS. 7-10 include a front view, a cross-sectional view, a first perspective view, and a second perspective view, respectively, of the second intramedullary plate of the preferred embodiment;

FIGS. 11-13 include a front view, a first perspective view, and a second perspective view, respectively, of the first and second intramedullary plates of the preferred embodiment in an engaged position;

FIGS. 16 and 17 include a side view and a cross-sectional view, respectively, of the fastener of the preferred embodiment;

DESCRIPTION OF THE PREFERRED EMBODIMENTS

Figure 7:
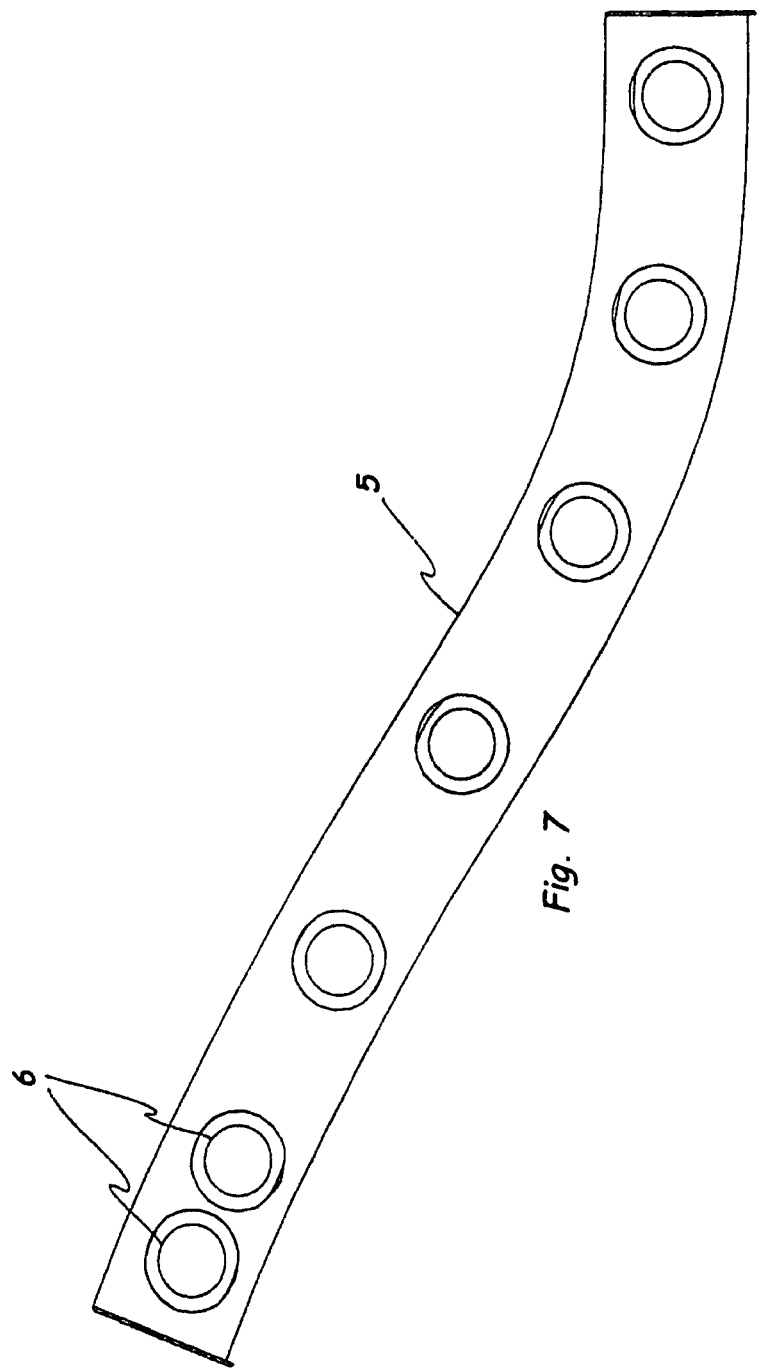
Figure 9:
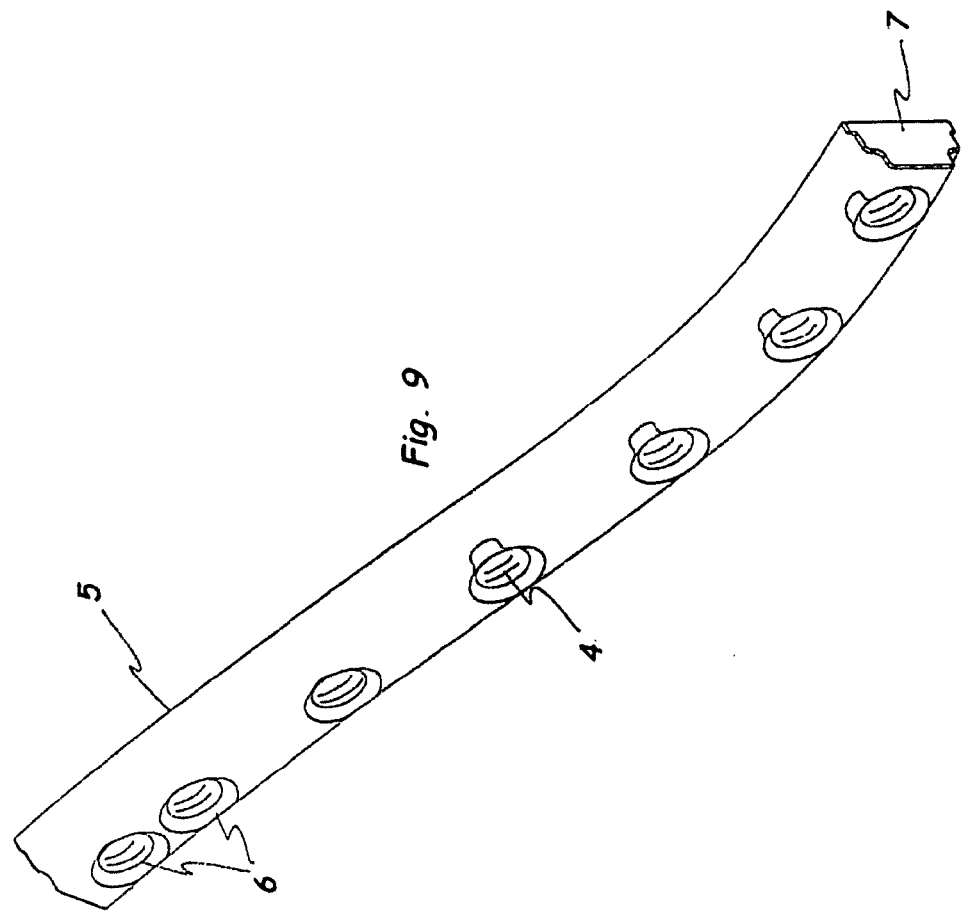
Figure 8:
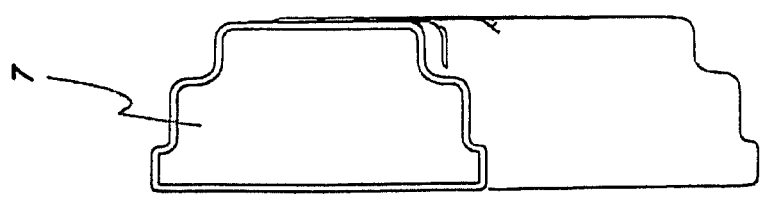

The following description of the preferred embodiments of the invention is not intended to limit the invention to these preferred embodiments, but rather to enable any person skilled in the art to make and use this invention.

As shown in FIGS. 1 and 2, the intramedullary locking system of the preferred embodiment includes a first intramedullary plate 1 with a plurality of first plate bores 2, a second intramedullary plate 5 with a plurality of second plate bores 6 that interfaces and is fastened to the first intramedullary plate 1, a plurality of fasteners 13 that fasten the first and second intramedullary plates 1 and 5 to bone through the first and second plate bores 2 and 6, and an alignment fixture 20 held outside of the body with a proximal fixture end 9 that corresponds with the proximal end of the bone 10 and a distal fixture end 11 that corresponds with the distal end of the bone 12. The first and second intramedullary plates 1 and 5 are preferably inserted into the marrow cavity of the fractured bone and then preferably fastened to each other and to the bone to fixate the bone into the desired arrangement for healing. The first and second intramedullary plates 1 and 5 are fixated to the bone by the plurality of fasteners 13. The alignment fixture 20 is preferably used to assist the surgeon in locating the first and second plate bores 2 and 6 from outside of the patient's body, allowing the surgeons to make minimal incisions into the patient's body to apply the fasteners 13 and to fasten the first and second intramedullary plates 1 and 5 to the fractured bone of the patient. This system and method for intramedullary bone fixation preferably allows for a minimally invasive process to adequately fixate a fractured bone for healing.

As shown in FIGS. 3-6, the first intramedullary plate 1 preferably includes an end with a cross section that contains a duct 3. The duct 3 may be a closed duct (similar to an "O" cross section) or may alternatively be an open duct (similar to a "C" cross section), but may be any other suitable shape. As shown in FIGS. 7-10, the second intramedullary plate 5 preferably includes an end with a cross section that contains duct-connecting geometry 7 that allows insertion into the duct 3 of the first intramedullary plate (as shown in FIGS. 9-13).

Figure 14:
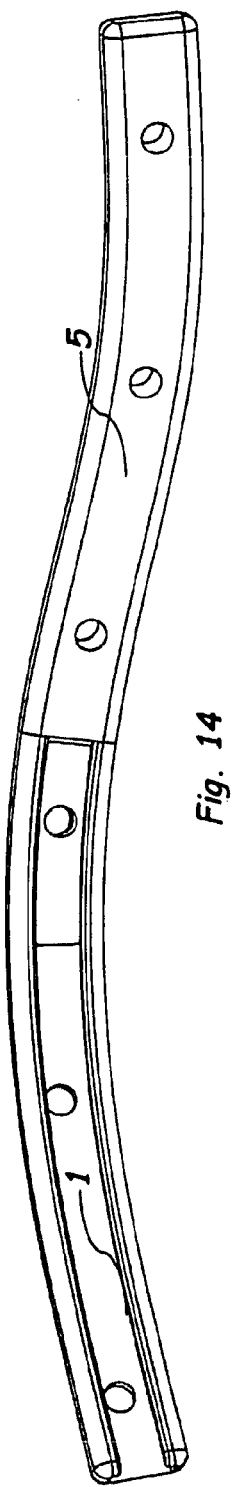
FIGS. 14 and 15 include a front view and a side view, respectively, of a variation of the first and second intramedullary plates of the preferred embodiment in the engaged position.
Figure 15:
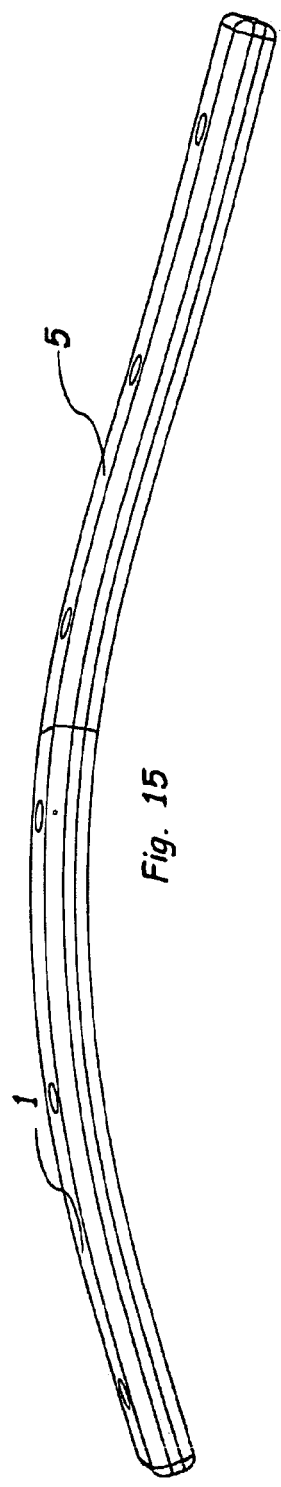

The geometry of the duct 3 and the duct-connecting geometry 7 also preferably align the first and second intramedullary plates 1 and 5 upon insertion. The duct 3 and the duct connecting geometry 7 may extend through the whole length of the first and/or second intramedullary plates 1 and 5 respectively (as shown in FIGS. 3-13), but may alternatively be contained to the interfacing ends of the first and second intramedullary plates 1 and 5 (as shown in FIGS. 14 and 15). The overlap of the first and second intramedullary plate 1 and 5 upon insertion preferably allows a first plate bore 2 and a second plate bore 6 to be in alignment such that a fastener 13 may be used to also fasten the first and second intramedullary plates 1 and 5 together. Alternatively, the first and second intramedullary plates 1 and 5 may include fastening geometry that fastens the first and second intramedullary plates 1 and 5 together upon engagement. For example, the first and second intramedullary plates 1 and 5 may include corresponding interlocking hooks, clamps, corresponding friction wedges, actuating hooks that are actuated by the surgeon upon insertion, spring loaded clasps, dovetail geometry, and/or screws and mating threads. The system of the preferred embodiments preferably includes one first intramedullary plate 1 installed on one side of the bone fracture that interfaces with one second intramedullary plate 5 installed on the other side of the bone fracture, but may alternatively include two first intramedullary plates 1 that each interface with end of one second intramedullary plate 5 (as shown in FIGS. 2 and 18-21). The preferred embodiments may alternatively include one first intramedullary plate 1 and two second intramedullary plates 5 wherein each end of the first intramedullary plate 1 interfaces with a second intramedullary plate 5. However, any combination of first and second intramedullary plates 1 and 5 suitable to the fracture type, bone type and geometry, and effective fracture healing may be used. The first and second intramedullary plates 1 and 5 may also include curves and bends that accommodate to the natural curvature of the fractured bone to facilitate effective bone fracture healing.

As shown in FIGS. 3-13, the first and second plate bores 2 and 6 preferably include bore threads 4 and the fasteners 13 preferably include fastener threads 8 (as shown in FIGS. 16 and 17) that mate with bore threads 5. The mating threads function to allow the fasteners 13 to fasten to the first and second plate bores 2 and 6 when fastening the first and second intramedullary plates 1 and 5 to the bone. The mating threads also preferably function to allow the fasteners 13 to fasten the first and second plate bores 2 and 6 together. The fasteners threads 8 are preferably of the type to self-tap into bone material, which functions to facilitate the process of fastening the first and second intramedullary plates 1 and 5 to the bone by eliminating the intermediary step of tapping the bone for fastening. The fasteners 13 may alternatively include self fastening geometry that engages the first and second plate bores 2 and 6 and bone upon insertion, for example, a plurality of wedges that are angled to allow the fastener 13 to be inserted into the bores 2 and 6 and the bone but prevent the fastener 13 to be loosened from the bores 2 and 6 and the bone under normal forces incurred during daily activities of the patient. The fasteners 13 may also include anchoring geometry that prevents relative movement between the intramedullary plates 1 and 5 and the bone and/or nut and bolt geometry. However, any other fastening geometry allowing the fasteners 13 to suitably fasten the first and second intramedullary plates 1 and 5 to the bone may be used.

Figure 18:
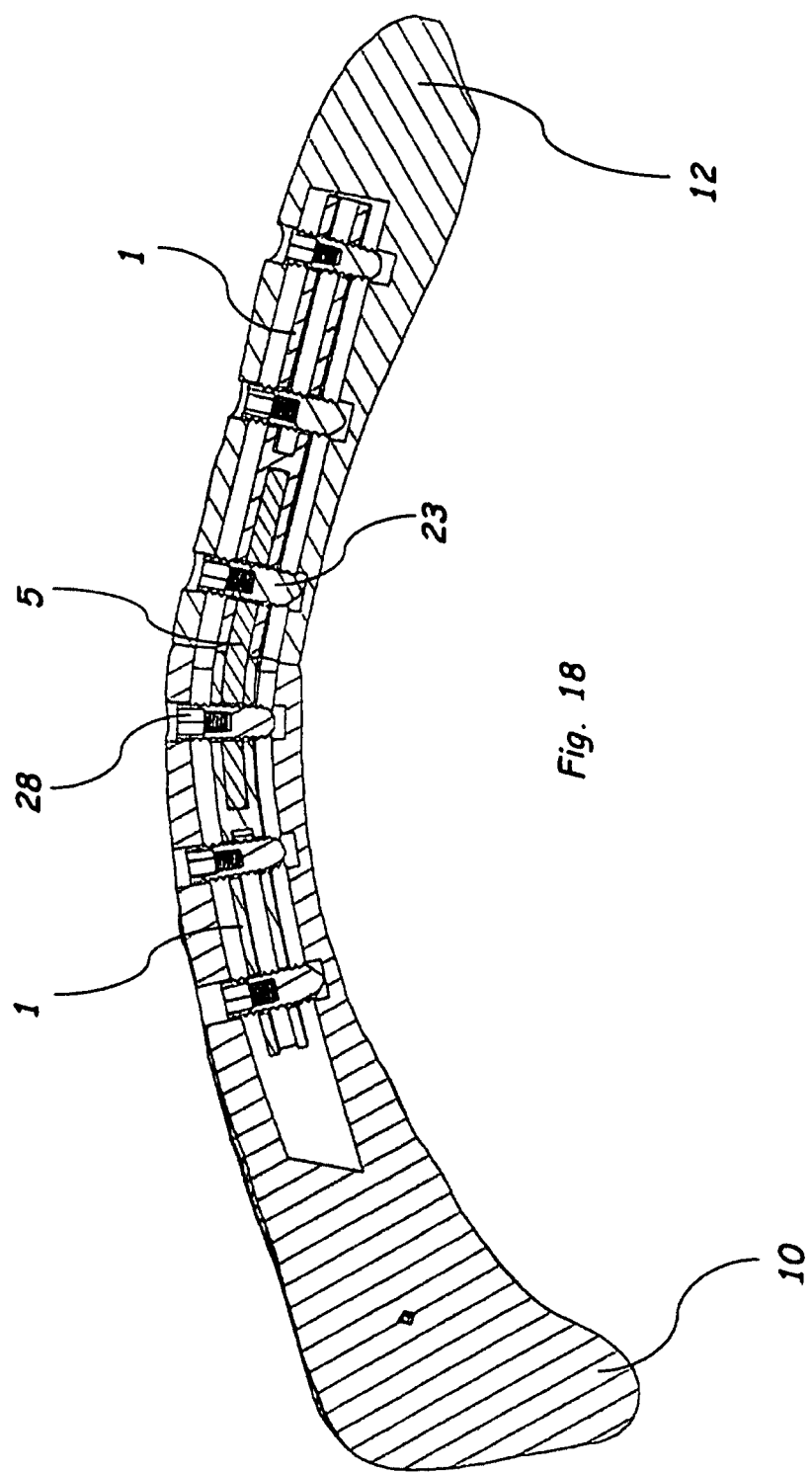
FIG. 18 is a schematic representation of the preferred embodiment in FIG. 1 when installation is complete in a cross section view.

As shown in FIGS. 16 and 17, the fasteners 13 preferably include a first fastener component 23 and a second fastener component 22. The first fastener component 23 preferably includes an outer wall with the fastener threads 8 and a tip closing the distal end 29 of the first fastener component, and an inner wall defining a bore with non-round geometry, preferably a hexagonal hole but may alternatively be of any other non-round geometry, opening the proximal end 28. The second fastener component 22 preferably includes a shaft with a proximal end 26 and a corresponding non-round geometry, preferably a hexagonal cross section but may alternatively be any other corresponding non-round geometry, on the distal end 27 that inserts into and engages with the inner wall of the first fastener component 23. The diameter of the shaft may be constant through the second fastener component 22 or may be variable. The first fastener component 23 preferably functions to remain within the body of the patient to fasten the first and second intramedullary plates 1 and 5 to the bone. The first fastener component 23 is preferably of a size that is comfortably contained within the circumference of the cross section of the fractured bone (as shown in FIG. 18), but may alternatively be of any size that is suitable to be contained within the body of the patient as the bone fracture progresses through the healing process. The second fastener component 22 preferably functions as a holder for the first fastener component 23 and facilitates the surgeon in aligning, placing, and engaging the first fastener component 22 into the bone and intramedullary plates 1 and 5. The first fastener component 23 preferably detaches from the second fastener component 22 once the first fastener component 23 is engaged into the bone and the first and second plate bores 2 and 6. The second fastener component 22 preferably further includes a knob on the proximal end 26. The knob functions to facilitate the surgeon in rotating the shaft of the second fastener component to subsequently engage the fastener threads 8 with the bone and the first and second plate bores 2 and 6 and to function as a locating element when used with the alignment fixture 20 (shown in FIGS. 1 and 2 and further described below). The second component 22 may also include a hexagonal indent geometry that allows the surgeon to temporarily engage a hex wrench to the second fastener component to achieve more leverage during engagement of the fastener 13. The hex wrench geometry may alternatively be included into the second fastener component 22. However, any other geometry suitable to assisting the surgeon in engaging the fastener 13 may be used. The first component 23 may alternatively contain any other fastening features suitable to engage the bone with the first and second intramedullary bores 2 and 6. The second component 22 may alternatively contain any other geometrical features suitable to facilitate engagement of the first fastener component 23.

The first fastener component 23 is preferably temporarily engaged with the second fastener component 22 through a third fastener component 21. The third fastener component 21 preferably includes a shaft with a stop on the proximal end 24 and third component threads on the distal end 25. The inner wall of the first fastener component 23 of this variation preferably also includes first component threads that match with the third component threads that are preferably distal to the non-round geometry and the second fastener component 22 preferably includes a channel that runs through the length of the shaft. The shaft of the third fastener component 21 is preferably of a diameter substantially equivalent to or less than the diameter of the channel in the second fastener component 22 while the stop is preferably of a diameter larger than the channel, allowing the third fastener component 21 to be inserted into the channel until the stop comes into contact with the second fastener component and prevents further insertion, and the length of the shaft is preferably longer than that of the second fastener component 22, allowing the third component threads to protrude beyond the corresponding non-round geometry of the second fastener component 22 when insertion is completed. Once inserted, the third component threads are engaged with the first component threads and the third component 21 functions to clamp the second component 22 to the first component 21, engaging the non-round geometry and the corresponding non-round geometry and allowing rotation of the second component 22 to cause rotation of the first component 21. Alternatively, the first and second fastener components 23 and 22 may be temporarily engaged using magnets that attract the first and second fastener components to each other, corresponding bayonet geometry, mating threads, pin and hole geometry (for example, a pin is inserted perpendicular to the shafts of the first and second fastener components 23 and 22 to engage the overlap between the two components), and/or snap geometry. However, any other fastening materials and methods suitable to temporarily engage the first and second fastener components 23 and 22, while allowing the movement of the second fastener component 22 to engage the first fastener component 23 to the bone and the first and second plate bores 2 and 6 may be used.

As shown in FIGS. 1, 2, and 19-21, the alignment fixture 20 of the preferred embodiments preferably includes a plurality of channels 30 that function to align the shaft of the second fastener component 22, and subsequently the first fastener component 23, with the first and second plate bores 2 and 6. The alignment fixture 20 is preferably arranged with the first and second intramedullary plates 1 and 5 such that the channels 30 are each coaxial with a first plate bore 2 and/or the second plate bore 6. The diameter of each of the channels 30 are preferably substantially equal to or larger than the diameter of the shaft of the second fastener component 23 to prevent excessive movement of the fastener 13 when inserted into the channel 30, thus maintaining a substantially coaxial relationship between the fastener 13 and the channels 30 upon insertion of the fastener 13. The diameter of the channels 30 may be constant through the length of the channel 30, but may also be variable to suitably interface with and align the fastener 13. Alternatively, the other features on the channel 30 and the fastener 13 may be used to align the fastener 13, for example, utilizing the contact surface between the knob of the second fastener component 22 and the channel 30. However, any other method to align the fastener 13 to the channel 30 and subsequently to the first and second plate bores 2 and 6 may be used. The channels 30 may also be in any other orientation suitable to align the fasteners 13 with the first and second plate bores 2 and 6.

In the preferred embodiments, because the channels 30 are each coaxial with a first plate bore 2 and/or the second plate bore 6, the insertion of a fastener 13 into a channel 30 aligns the fastener 13 with a first plate bore 2 and/or the second plate bore 6 and facilitates the surgeon in engaging the fasteners 13 with the bone and the first and second intramedullary plates 1 and 5. The knob of the second fastener component 22 functions as a stop and as a depth locating feature for the fastener 13. The knob is preferably of a diameter larger than the diameter of the channel 30 to prevent excessive insertion of the fastener 13 when engaging with the bone and the first and second intramedullary plates 1 and 5. The fastener 13 is inserted into the channel 30 for alignment until the fastener 13 comes into contact with the bone. The shaft of the second fastener component 22 is then preferably rotated to allow the fastener threads 8 to self tap into the bone and engage with the first and second plate bores 2 and 6. The fastener 13 moves downward into the channel 30 as the fastener threads 8 screw into the bores 2 and 6 until the knob comes into contact with the alignment fixture 20. This prevents the fastener 13 from tapping too far into the bone and reliably aides the surgeon in determining the depth of the insertion of the fastener 13 to adequately engage the first and second intramedullary plates 1 and 5 with the bone. This method of locating, alignment, and depth determination when engaging the fastener 13 allows the surgeon enough confidence that sufficient engagement is achieved without the need for visible verification, allowing minimal incisions to be made in the patient's body. However, any other method suitable to locate, align, and engage the fastener 13 may be used.

Figure 20:
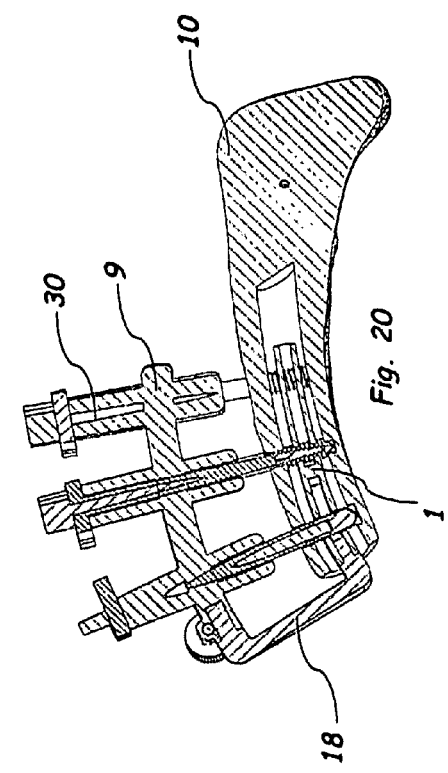
FIGS. 19-22 are various views of the preferred embodiment during installation.
Figure 19:
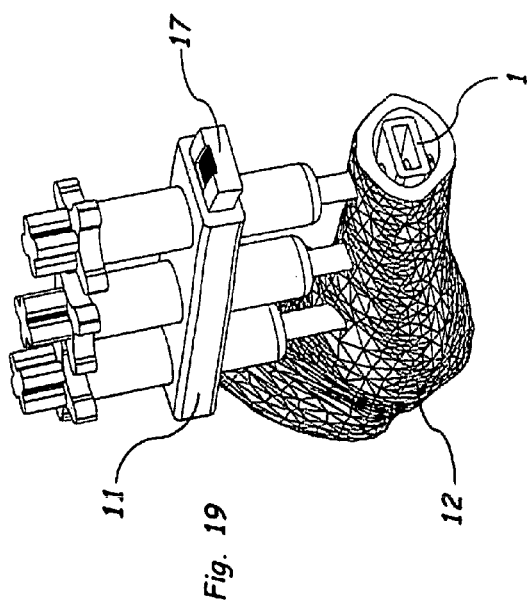

The alignment fixture 20 may include a first alignment portion 32 that corresponds with one section of the bone fracture and, and subsequently the first intramedullary plate 1, and a second alignment portion 34 that corresponds with another section of the bone fracture, and subsequently the second intramedullary plate 5 (or an additional first intramedullary plate 1 if a plurality of first intramedullary plates 1 are used). This variation of the alignment fixture 20 preferably includes a temporary holder 18 (as shown in FIG. 20) that functions to align the first alignment portion 32 with the first intramedullary plate 1, allow a fastener 13 to be inserted into a channel 30 of the first alignment portion 32 and engaged with the bone and the first intramedullary plate 1 and allowing the temporary holder 18 to be removed without disturbing the relative positions of the first alignment portion 32 and the first intramedullary plate 1. The fastener 13 and the alignment fixture 20 preferably also include geometry that prevents the alignment fixture 20 from sliding along the shaft of the second fastener component 22 and maintaining the alignment position until all fasteners 13 have been engaged. The temporary holder 18 is then preferably used to align the second alignment portion 34 to the second intramedullary plate 5 (and/or an additional first intramedullary plate 1) and the process of engaging fasteners 13 is repeated. The temporary holder 18 for the second alignment portion 34 may be identical to the temporary holder 18 for the first alignment portion 32, but may alternatively be of a different geometry to accommodate different geometries of the second alignment portion 34 and intramedullary plate. Once the fasteners 13 on the second alignment portion 34 are engaged, the temporary holder 18 is removed and the intramedullary plates of the two portions of the bone fracture are fastened to each other using additional fasteners 13 and/or an additional intramedullary plate and assisted by aligning the first and second portions 32 and 34 and using the locating tab 17 and alignment knob 19.

Figure 21:
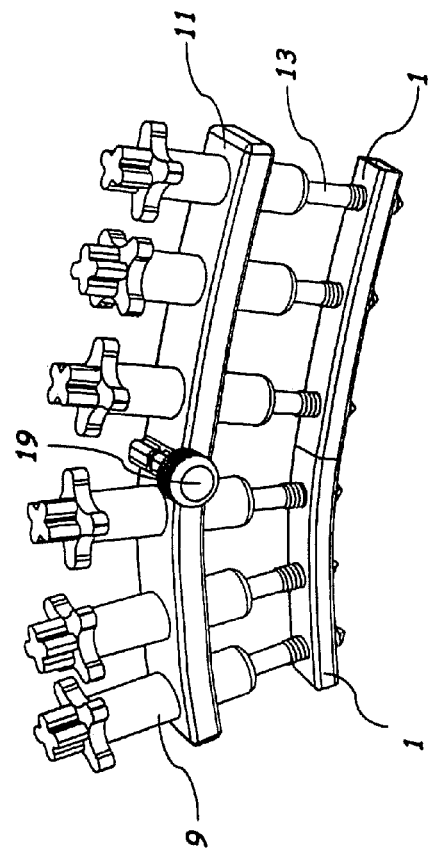
Figure 22:
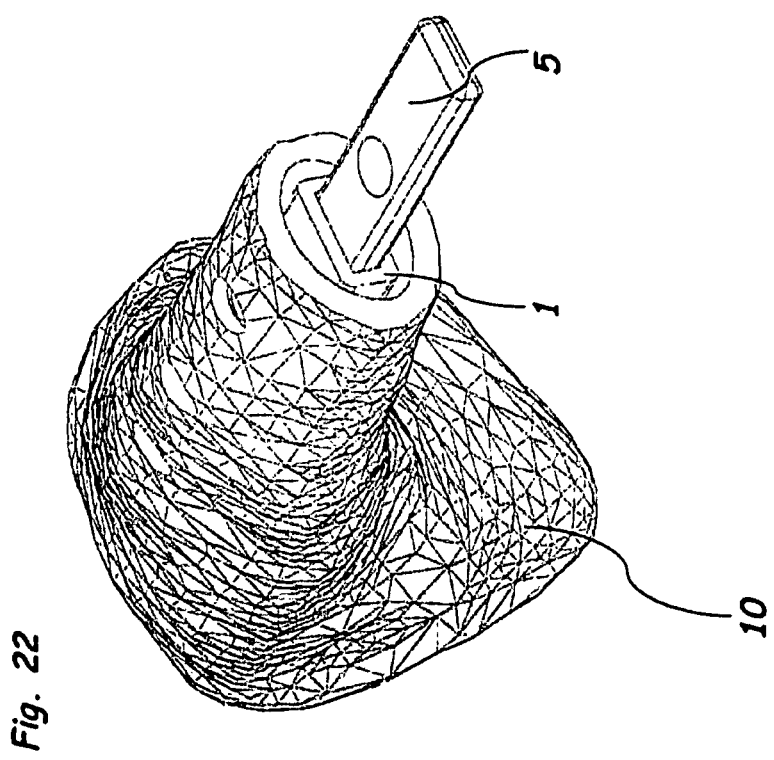

Alternatively, once fasteners 13 are engaged in the first alignment portion 32, the second intramedullary plate 5 is engaged with the first intramedullary plate 1 (as shown in FIG. 22). In the variation with a plurality of first intramedullary plates 1, the additional first intramedullary plate 1 is then engaged with the other end of the second intramedullary plate 5. As shown in FIG. 21, the second alignment portion 34 is then preferably temporarily engaged and aligned with the first alignment portion 32 using a tab 17 and is tightened with an alignment knob 19 that engages the tab 17 such that the second alignment portion 34 are aligned with the second intramedullary plate 5 (or the additional first intramedullary plate 1). Fasteners 13 are inserted into the channels 30 of the second alignment portion and engaged with the second intramedullary plate 5 (and/or the additional first intramedullary plate 1). However, any other method, component, and arrangement suitable to align the alignment fixture 20 with the first and second intramedullary plates 1 and 5 while allowing the fasteners 13 to be engaged to the bone and the first and second plate bores 2 and 6 may be used.

Once all the fasteners 13 have been engaged using the alignment fixture 20, the second fastener component 22 is disengaged from the first fastener component 23, subsequently disengaging the alignment fixture 20 from the first and second intramedullary plates 1 and 5, leaving the first fastener components 23 contained within the circumference of the body and allowing the surgeon to suture up the relatively small incisions made in the patient.

As a person skilled in the art will recognize from the previous detailed description and from the figures and claims, modifications and changes can be made to the preferred embodiments of the invention without departing from the scope of this invention defined in the following claims.

We claim:

1. A system for the intramedullary fixation of a fractured bone in a body comprising:
    a first intramedullary plate having a first geometry and defining a plurality of first plate bores;
    a second intramedullary plate having a second geometry and defining a plurality of second plate bores, wherein the second intramedullary plate interfaces and is fastened to the first intramedullary plate;
    a plurality of fasteners configured to fasten the first and second intramedullary plates to the bone; and
    an alignment fixture held outside of the body that indicates the location of the bores of the first and second intramedullary plates and through which the fasteners are aligned with the bores of the first and second intramedullary plates;
    wherein the bores of the first and second intramedullary plates and the fasteners include mating threads; and
    wherein the fasteners include a first fastener component and a second fastener component, wherein the first fastener component has an outer wall having the threads and closing a distal end of the first fastener component and has an inner wall defining a non-round geometry and opening a proximal end of the first fastener component, wherein the second fastener component includes a shaft with a knob on a proximal end of the second fastener component and a cross-section that inserts into and engages with the inner wall of the first fastener component on a distal end of the second fastener component.

2. The system of claim 1 wherein the first fastener component is of a length that is configured to be contained within the diameter of the bone when fully engaged.

3. The system of claim 1 wherein the fasteners further include geometry to temporarily fasten the first and second fastener components to each other selected from the group consisting of: bayonet geometry, mating threads, pin and hole geometry, peg and track geometry, snap enclosure geometry, and magnets.

4. The system of claim 1 wherein the second fastener component includes a channel through the shaft; the fastener further includes a third fastener component that contains a third component shaft to be inserted into the channel of the second component that is of a length longer than the shaft of the second fastener component and a diameter smaller than the diameter of the channel of the second fastener component and that includes a stop on the proximal end with a diameter larger than the diameter of the channel and a threaded portion on the distal end; wherein the inner wall of the first fastener component further includes a threaded portion on the distal end that mates with the threaded portion on the shaft of the third fastener component; wherein the insertion of the third fastener component through the shaft of the second fastener component and the engagement of the threads of the third fastener component with the inside threads of the first fastener components clamps the second component to the first component and temporarily fastens the three fastener components together.

5. The system of claim 1 wherein the alignment fixture includes a plurality of channels, each through which a fastener is inserted, wherein the channels maintain a substantially coaxial relationship between each fastener and a bore and wherein the diameter of the channel is smaller than the diameter of the knob of the second fastener component, preventing the fastener from passing through the channel.

6. The system of claim 1 wherein the alignment fixture includes a first alignment portion configured to correspond with one section of the bone fracture, a second alignment portion configured to correspond with another section of the bone fracture, and a fastening mechanism to selectively fasten the first portion to the second portion.

7. The system of claim 6 wherein the fastening mechanism includes a knob on the second portion and a tab protruding from the first portion, wherein the knob and tab are selectively engagable with each other.

8. The system of claim 1 wherein the alignment fixture includes a temporary holder that aligns the alignment fixture with the first and second intramedullary plates to allow the fasteners to be installed into the bores of the first and second intramedullary plates and fastening the first and second intramedullary plates to bone.

9. The system of claim 1 wherein the system includes a combination of first and second intramedullary plates such that the difference between the number of first intramedullary plates and the number of second intramedullary plates is either zero or one.

10. The system of claim 9 wherein the first and second intramedullary plates are arrangeable within the intramedullary canal of a fractured bone in an arrangement selected from the group consisting of: (a) a first intramedullary plate insertable into one section of the fractured bone and a second intramedullary plate is insertable into another section of the fractured bone, (b) a first intramedullary plate insertable into one section of the fractured bone and another first intramedullary plate insertable into another section of the fractured bone, and (c) a second intramedullary plate insertable into one section of the fractured bone and another second intramedullary plate insertable into another section of the fractured bone.

11. The system of claim 9 wherein the first intramedullary plate has a cross-section that contains a duct and the second intramedullary plate includes an end with a cross-section allowing insertion into the duct of the first intramedullary plate, wherein the insertion facilitates an alignment between the first intramedullary plate and the second intramedullary plate in a predetermined orientation with a first plate bore coaxial with a second plate bore.

12. The system of claim 11 wherein the duct is of a cross-section selected from the group consisting of: a "C" type cross-section, and an "O" type cross-section.

13. The system of claim 11 wherein the fasteners also fasten the first and second intramedullary plates together in the aligned position.

14. The system of claim 1 wherein the fasteners include geometry configured to fasten the first and second intramedullary plates to bone selected from the group consisting of: self fastening wedges that allow insertion of the fastener but not extraction under loads experienced during use of the bone, anchoring geometry that prevents movement of the intramedullary plates relative to the bone, and nut and bolt geometry.

15. The system of claim 1 wherein the fastener includes self-tapping threads that are configured to self-tap into bone material.

\* \* \* \* \*